United States Patent [19]

Comstock

[11] 4,373,915
[45] Feb. 15, 1983

[54] IATROGENIC SHIELD

[76] Inventor: Herold E. Comstock, Rte. 4, Box 35-A, Winchester, Va. 22601

[21] Appl. No.: 316,994

[22] Filed: Nov. 2, 1981

[51] Int. Cl.³ .............................................. A61C 5/14
[52] U.S. Cl. ..................................... 433/136; 433/139
[58] Field of Search ........................... 433/136, 40, 139

[56] References Cited

U.S. PATENT DOCUMENTS

| 388,620 | 8/1888 | Booth | 433/149 |
| 638,973 | 12/1899 | Mehlig | 433/40 |
| 1,321,451 | 11/1919 | Ivory | 433/139 |

Primary Examiner—Robert Peshock
Attorney, Agent, or Firm—Shenier & O'Connor

[57] ABSTRACT

An iatrogenic shield which includes a resilient band of stainless steel having a front portion which is placed against the interproximal surface of a tooth to protect it from inadvertent contact with dental instruments. Two side portions contract against the buccal and lingual surfaces of the tooth to hold the shield in place and each include permanent loops used for placement and removal of the shield. The front portion may also include a recess along its gingival edge and a lip along its occlusal edge.

6 Claims, 3 Drawing Figures

IATROGENIC SHIELD

FIELD OF THE INVENTION

My invention relates to the field of protecting adjacent tooth structure during dental procedures and more particularly to a shield adapted to prevent iatrogenic carious lesions.

BACKGROUND OF THE INVENTION

The preparation of a carious lesion for restoration normally requires the use of a dental handpiece burr or other cutting instrument by a dentist. Often the dentist may inadvertently cause positive contact of the dental burr with adjacent healthy tooth structure, causing damage at the surface. As it is accepted that the first step in dental decay is the abrasive one, caused either chemically or mechanically, this accidental damage may well lead to a new carious lesion. In fact, it has been established that between ten and twenty percent of new carious lesions occurring on the interproximal surfaces of teeth are iatrogenic.

Swan-Gett et al. U.S. Pat. No. 3,772,790 issued Nov. 20, 1973, discloses a tooth isolating shield formed by a semi-rigid easily cut covering which is adapted to fit over the upper and lower teeth of the patient, covering the entire mouth area. The shield is then cut by the dentist to expose the teeth or tooth to be worked on. While this shield effectively isolates the tooth or teeth being worked on, keeping the work area uncontaminated and protecting mouth tissue and other teeth from contamination, it does not provide protection from injury to the interproximal surfaces of adjacent teeth as the covering only extends over the labial or buccal, occlusal and lingual surfaces of the adjacent teeth. In addition, as the covering must be formed from easily cut material so that the dentist may readily expose the teeth to be worked on, it obviously cannot afford a high level of protection against injury to the teeth and mouth from inadvertent positive contact with the dental burr or other cutting instruments.

SUMMARY OF THE INVENTION

One object of my invention is to provide an iatrogenic shield which is simple in design and construction, and economical for its one time intended use and throwaway purpose.

Another object of my invention is to provide an iatrogenic shield which is small, thin and lightweight, thus not interfering with nor obstructing the dental operation.

Still another object of my invention is to provide an iatrogenic shield which may be quickly and easily placed in the desired position.

A further object of my invention is to provide an iatrogenic shield which is not easily accidentally dislodged from its desired location.

A still further object of my invention is to provide an iatrogenic shield which reduces dental costs by impeding abrasions to the adjacent dentition to prevent the first phase of tooth decay.

Other and further objects of my invention will appear from the following description.

BRIEF DESCRIPTION OF THE DRAWINGS

In the accompanying drawings in which reference is made in the instant specification and which are to be read in conjunction therewith and in which like reference characters are used to indicate like parts in the various views.

DESCRIPTION OF THE PREFERRED EMBODIMENT

Figure 1:
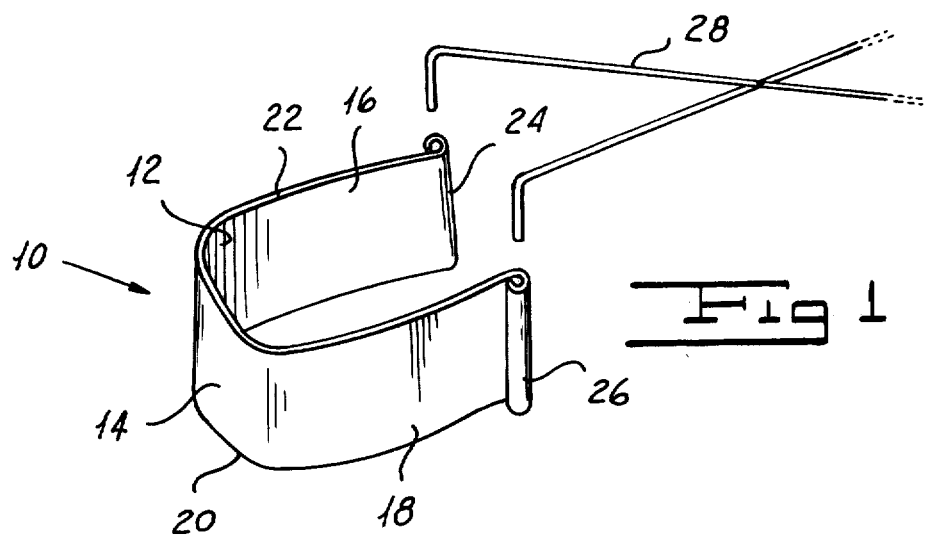
FIG. 1 is a perspective view of my iatrogenic shield.

Referring now to FIG. 1 of the drawings, my iatrogenic shield, indicated generally by the reference character 10, includes a "U" shaped band or clamp having an inner surface 12 to be placed against the tooth to be protected, formed from a distal or front wall 14 and a pair of sidewalls 16 and 18 all having a common gingival edge 20 and occlusal edge 22. Sidewalls 16 and 18 are adapted to contract against the buccal and lingual surfaces of the tooth, and both are formed with respective permanent loops 24 and 26 which may receive the gripping ends of tongs 28 or cotton pick-ups, to assist in the placement and removal of the shield 10.

My shield is formed from a lightweight material, such for example as stainless steel, not easily penetrated by a dental burr, and having sufficient elasticity to resume its normal shape after deformation as necessary to effect placement. In addition, my shield is sufficiently thin to pass between the interproximal surfaces of adjacent teeth.

Figure 2:
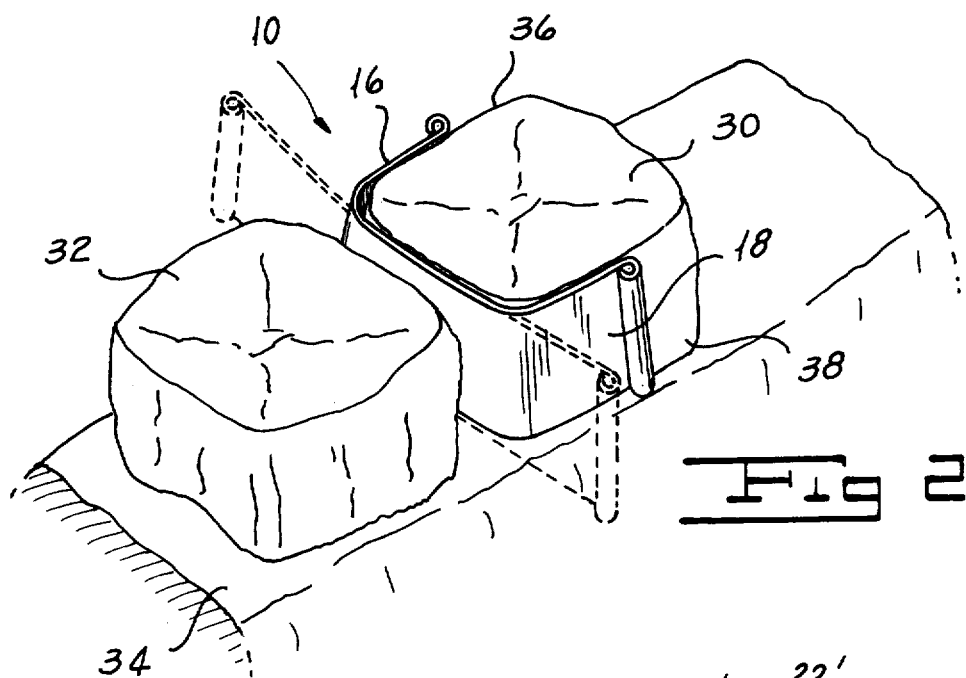
FIG. 2 is a fragmentary perspective view of a patient's jaw, with my iatrogenic shield shown between two teeth.

Referring now to FIG. 2, my shield may be deformed to the position indicated by the broken lines to permit its placement between the interproximal surfaces of the tooth 32 to be operated on, and the adjacent tooth 30, both having an associated gum 34. Once the shield is properly positioned and released, it will revert back to its original shape, with sidewalls 16 and 18 hugging the buccal surface 36 and lingual surface 38 of tooth 30. It is necessary of course to use different size shields for different size teeth to insure a proper fit and to guard against dislodgment of the shield. It should also be noted that my shields are intended for a one-time use and may be disposed of thereafter.

Figure 3:
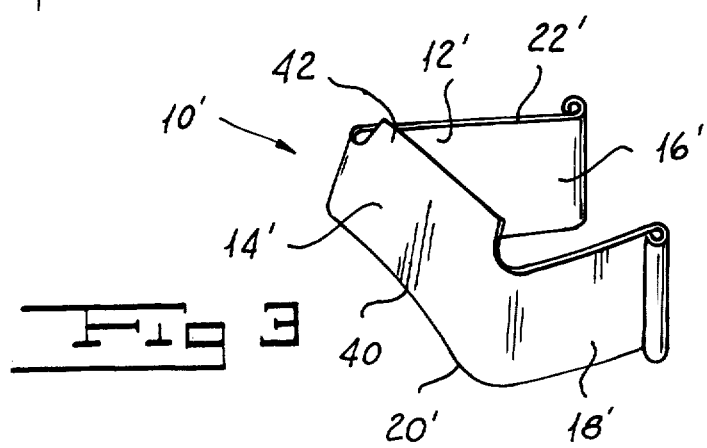
FIG. 3 is a perspective view of a second embodiment of my iatrogenic shield.

Referring now to FIG. 3, a second embodiment of my invention again includes a "U" shaped clamp 10' having an inner surface 12' to be placed against the tooth to be protected, formed from a distal wall 14' and sidewalls 16' and 18' all having a common gingival 20' and occlusal 22' edge.

I form a recess 40 along the gingival edge 20' of the distal wall 14', adapted to be conformingly received by the natural curve of the gums, so that my shield 10' may fit more snugly against the protected tooth. I also form a lip 42 along the occlusal edge 22' of the distal wall 14', angled toward the inner surface 12' to protect the biting surface of the protected tooth.

It will be seen that I have accomplished the objects of my invention. I have provided an iatrogenic shield which is simple in design and construction and economical for its one-time intended use and throwaway purpose. My shield is small, thin and lightweight and does not interfere not obstruct the dental operation. My shield may be quickly and easily placed in the patient's mouth and is not easily accidentally dislodged. In addition, my shield reduces dental costs by impeding abrasions to the adjacent dentition to prevent the first phase of tooth decay.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention what I claim is:

1. A shield comprising a resilient band having a front portion adapted to be placed against the interproximal surface of a tooth and two side portions, said band being biased so that said side portions hug the buccal and lingual surfaces of said tooth, and loops at the ends of said sides for receiving elements of a tool adapted to spread said sides to facilitate placement and removal of said shield.

2. A shield comprising a resilient band having a front portion adapted to be placed against the interproximal surface of a tooth and two side portions, said front portion having a recess along its gingival edge and a lip along its occlusal edge, said band being biased so that said side portions hug the buccal and lingual surfaces of said tooth, said side portions including means for facilitating placement and removal of said shield by use of a suitable tool.

3. A shield comprising a resilient band having a front portion adapted to be placed against the interproximal surface of a tooth and two side portions, said band being biased so that said side portions hug the buccal and lingual surfaces of said tooth, said side portions including means for facilitating placement and removal of said shield by use of a suitable tool.

4. A shield comprising a resilient band having a front portion adapted to be placed against the interproximal surface of a tooth and two side portions, said front portion having a recess along its gingival edge, said band being biased so that said side portions hug the buccal and lingual surfaces of said tooth.

5. A shield comprising a resilient band having a front portion adapted to be placed against the interproximal surface of a tooth and two side portions, said front portion having a lip along its occlusal edge, said band being biased so that said side portions hug the buccal and lingual surfaces of said tooth.

6. A shield comprising a resilient band having a front portion adapted to be placed against the interproximal surface of a tooth and two side portions, said band being biased so that said side portions hug the buccal and lingual surfaces of said tooth.

* * * * *